United States Patent [19]

Bara

[11] Patent Number: 5,972,318
[45] Date of Patent: Oct. 26, 1999

[54] TRANSFER-FREE MAKE-UP OR CARE COMPOSITION CONTAINING ALKYLPOLYSILOXANE

[75] Inventor: Isabelle Bara, Paris, France

[73] Assignee: L'Oreal, Paris, France

[21] Appl. No.: 08/871,430

[22] Filed: Jun. 9, 1997

[30] Foreign Application Priority Data

Jun. 7, 1996 [FR] France .................................. 96 07107

[51] Int. Cl.$^6$ .................................... A61K 7/025
[52] U.S. Cl. ................. 424/64; 424/63; 424/69; 424/78.03; 424/401; 424/DIG. 5
[58] Field of Search ................. 424/401, 78.03, 424/64, 63, 69, DIG. 5

[56] References Cited

U.S. PATENT DOCUMENTS

| | | | |
|---|---|---|---|
| 4,423,041 | 12/1983 | Clum et al. | 424/184 |
| 5,288,482 | 2/1994 | Krzysik | 424/641 |
| 5,334,737 | 8/1994 | Thimineur et al. | 556/440 |
| 5,478,555 | 12/1995 | Bara et al. | 424/78.03 |
| 5,496,544 | 3/1996 | Mellul et al. | 424/78.03 |

FOREIGN PATENT DOCUMENTS

| | | |
|---|---|---|
| A 0521647 | 1/1993 | European Pat. Off. . |
| A 0530085 | 3/1993 | European Pat. Off. . |
| A 0602905 | 6/1994 | European Pat. Off. . |
| A 2688134 | 9/1993 | France . |
| WO A 9640044 | 12/1996 | WIPO . |

*Primary Examiner*—Jyothsna Venkat
*Attorney, Agent, or Firm*—Finnegan, Henderson, Farabow, Garrett & Dunner, L.L.P.

[57] ABSTRACT

A transfer-free composition, in particular, an anhydrous composition in stick form, containing (a) at least one silicone which is volatile at ambient temperature, which at least one silicone comprises a silicone structure and at least one unit containing at least one alkyl chain which is pendent and/or at the end of the silicone structure, the at least one chain being linear or branched with 3 to 10 carbon atoms, and (b) at least one silicone wax which is solid or semisolid at ambient temperature, which at least one silicone wax comprises a silicone structure and at least one unit containing at least one alkyl or alkoxy chain which is pendent and/or at the end of the silicone structure, the at least one chain being linear or branched with 10 to 45 carbon atoms. This composition can be a lip care or make-up composition or a foundation composition for the make-up of both the face and the human body.

43 Claims, No Drawings

TRANSFER-FREE MAKE-UP OR CARE COMPOSITION CONTAINING ALKYLPOLYSILOXANE

The present invention relates to a composition for the care and/or the make-up of the skin and/or the lips, and in particular a lip rouge in stick form or a foundation in stick or emulsion form.

Lip rouge and foundation compositions generally include fatty substances such as oils, pasty compounds and waxes, and a particulate phase generally composed of fillers and pigments. When applied to the skin or the lips, these compositions exhibit the disadvantage of transferring, i.e., being deposited at least partially, i.e., leaving a mark, on some substrates with which they can come into contact, especially a glass, a cup, a garment or the skin. This results in a mediocre durability of the film on the skin or on the lips, which makes it necessary to renew application of the foundation or lip rouge composition at regular intervals. Furthermore, the appearance of unacceptable marks on some garments and especially on blouse collars can inhibit some women from employing make-up of this type.

Linked with this disadvantage of transfer of the lip rouge compositions of the prior art, it is also necessary to note the awkward tendency of the films of these compositions to be dissolved by some cooked dishes and especially by dishes containing vegetable oils (in particular salads with vinaigrette dressing).

Another disadvantage of the lip rouge compositions of the prior art lies in the migration of these compositions, i.e., in the tendency of these compositions to spread within wrinkles and small wrinkles of the skin which surround the lips, resulting in an unaesthetic effect.

For a number of years many cosmeticians have taken interest in lip rouge compositions and, more recently, in foundation compositions which are "transfer-free". Thus, the company Shiseido has envisaged in its patent application JP-A-61-65809 "transfer-free" lip rouge compositions containing from 1 to 70% by weight of liquid silicone resin containing silicate repeating units (or containing a three-dimensional network) containing alkyl pendent chains of 1 to 6 carbon atoms, or phenyl ones, from 10 to 98% by weight of a volatile silicone oil containing a cyclic Si—O chain and containing methyl radicals and pulverulent fillers. These compositions, while entirely satisfactory with respect to the "transfer-free" property, have the disadvantage of being liquid and therefore not very convenient to employ, or at least far from the conventional concept of a lipstick, limiting the number of women likely to employ this type of lip rouge. In addition, the film obtained on the lips after evaporation of the silicone oil has the disadvantage of becoming uncomfortable in the course of time (drying out and pulling sensation), again inhibiting a certain number of women from employing lip rouge of this type. Nonvolatile silicone or other oils could be added to improve the comfort of this type of composition, but in this case some of the "transfer-free" effectiveness is lost.

More recently the Revlon company has envisaged in its patent application EP-A-602905 "nontransfer" lip rouges containing a volatile silicone which is cyclic or linear and contains pendent methyl chains and a silicone resin containing a pendent esterified chain containing at least 12 carbon atoms. This film of lip rouge again has the disadvantage of lacking comfort on application and especially of being too dry.

The subject-matter of the present invention is a care or make-up composition which makes it possible to overcome these disadvantages and possible, in particular, to obtain a film that does not transfer, does not migrate and that has cosmetic properties which are improved in relation to those of the "transfer-free" products of the prior art, especially with respect to the properties of slip, of not pulling and of not drying out the lips.

The present invention applies not only to lip make-up products but also to lip care products and to make-up and care products for the skin, such as foundations. In fact, the make-up products for the face exhibit the same disadvantage of "transfer" onto a substrate as the lip rouges.

Thus, the subject-matter of the present invention is a transfer-free make-up or care composition containing (a) at least one silicone which is volatile at ambient temperature, which at least one silicone comprises a silicone structure and at least one unit containing at least one alkyl chain which is pendent and/or at the end of the silicone structure, wherein the at least one alkyl chain is linear or branched and contains from 3 to 10 carbon atoms, and (b) at least one silicone wax which is solid or semisolid at ambient temperature, which at least one silicone wax comprises a silicone structure and at least one unit containing at least one alkyl or alkoxy chain which is pendent and/or at the end of the silicone structure, wherein the at least one chain is linear or branched and contains from 10 to 45 carbon atoms.

The composition of the invention has the advantage of possibly being in solid form and, for example, in the form of a stick. In addition, the composition of the invention makes it possible to obtain a film which is homogeneous, easy to apply and which spreads easily and uniformly. The film obtained also has a light texture and remains comfortable, not dry, and can be worn throughout the day. Advantageously, the composition of the invention is in anhydrous form.

The use of a silicone wax containing an alkyl chain and of polymeric nature contributes some elasticity to the film, making it more comfortable. In addition, the combined use of a volatile silicone and a silicone wax, both containing an alkyl chain, ensures good compatibility and good homogeneity of the mixture when the composition is being manufactured, without exuding oil (in the case where oil is present) or crystallization of wax during the manufacture and in the course of time. In addition, this combined use of alkylated silicones makes it possible to introduce into the composition both hydrocarbon adjuvants and silicone adjuvants containing linear or branched alkyl chains, like copolymers, and hence to adapt the properties of the film, especially insofar as the comfort on the lips or the skin of human beings is concerned. The adjuvants must, of course, not be detrimental to the homogeneity, the stability and the "nontransfer" property of the composition.

The composition of the invention may preferably include a particulate phase, generally present in a proportion of 0 to 35% of the total weight of the composition, preferably 5 to 25%, and which can include pigments and/or mothers-of-pearl and/or fillers usually employed in cosmetic compositions.

Pigments should be understood to mean inorganic or organic, white or colored particles which are insoluble in the wax and the volatile silicone and intended to color and/or opacify the composition. Fillers should be understood to mean lamellar or nonlamellar, inorganic or synthetic, colorless or white particles. Mothers-of-pearl should be understood to mean iridescent particles produced especially by certain mollusks in their shell, or else synthesized. These fillers and mothers-of-pearl are used to modify the texture of the composition and the matteness/gloss effect.

The pigments may be present in the composition in a proportion of 0 to 25% of the weight of the final composition, and preferably in a proportion of 5 to 15%. As inorganic pigments which can be employed in the invention there may be mentioned titanium, zirconium or cerium oxides and zinc, iron or chromium oxides and ferric blue. Among the organic pigments which can be employed in the invention there may be mentioned carbon black and barium, strontium, calcium and aluminum lakes.

The mothers-of-pearl may be present in the composition in a proportion of 0 to 20% of the total weight of the composition, preferably in a high content of the order of 8 to 15%. Among the mothers-of-pearl which can be employed in the invention there may be mentioned mica coated with titanium oxide, iron oxide, natural pigment or bismuth oxychloride, such as colored titanium mica.

The fillers may be present in a proportion of 0 to 35% of the total weight of the composition, preferably 5 to 15%. Talc, mica, silica, kaolin, powdered nylon (especially ORGASOL) and polyethylene, Teflon, starch, boron nitride, microspheres of copolymers such as EXPANCEL (Nobel Industries), POLYTRAP (Dow Corning) and microbeads of silicone resin (for example Toshiba TOSPEARLS) may be mentioned in particular.

The composition according to the invention can be manufactured conventionally by heating a mixture of a paste of one or more waxes, of one or several volatile silicones and optionally one or more pigments, one or more fillers and/or one or several other additives at a temperature which is higher than the highest melting temperature of the waxes, and then casting the molten mixture in a mold. This process makes it possible to obtain a composition in a solid form, i.e., in the form of a stick or of a small dish.

The present composition can also be obtained by extrusion, as described in European Patent Application EP-A-667 146, the disclosure of which is hereby incorporated by reference. This process involves blending the paste (waxes+volatiles+additives) during the cooling to create, in the bulk, regions of crushing of the paste with the aid of a roll mill or of a screw mixer-extruder. This process makes it possible to obtain a composition in the form of soft paste.

A volatile silicone containing an alkyl chain is intended to mean a silicone oil containing an alkyl chain and capable of evaporating on contact with the skin or the lips. These volatile silicones have the advantage of not having a flash point that is too low (higher than 40° C.), limiting the risks of ignition when compared with some cyclic volatile silicones, of being soft in application, odorless and above all tasteless, which is very important for an application to lips.

In particular, the volatile silicones of the invention have a $C_3$–$C_{10}$ pendent alkyl chain and/or a $C_7$–$C_{10}$ alkyl end chain.

The volatile silicones of the composition of the invention have in particular the following formula (I):

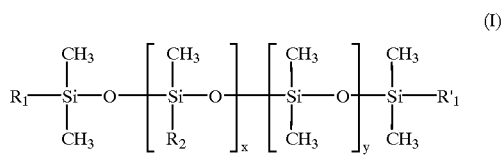

in which $R_1$, $R'_1$ and $R_2$ denote, independently of one another, a methyl group or hydrogen or a linear or branched chain containing from 3 to 10 carbon atoms, x and y independently denote an integer ranging from 0 to 10, on condition that x is other than 0 when $R_1$ and $R'_1$ denote the methyl group or hydrogen with $R_2$ other than methyl or hydrogen and that $R_1$ or $R'_1$ is other than the methyl group or hydrogen when $R_2$ denotes a methyl group or hydrogen or when x has the value 0. $R_2$ advantageously denotes a $C_3$–$C_{10}$ alkyl chain when $R_1$ and $R'_1$ each denote a methyl chain and when x is other than 0.

In particular, $R_2$ denotes a propyl, butyl, pentyl, hexyl, heptyl or octyl chain when $R_1$ and $R'_1$ each denote a methyl chain and x denotes 1, 2, 3 or 4, preferably 1, and y denotes 0, 1, 2, 3, 4, and preferably 0.

Another advantageous solution is the presence of $R_1$ and/or $R'_1$ in the form of a $C_7$—$C_7$ alkyl chain, especially with x having the value 0 and/or $R_2$ being methyl.

Among the volatile silicones that can be employed in the invention, there may be mentioned alkylheptamethyltrisiloxanes with a $C_4$, $C_5$, $C_6$, $C_7$ and $C_8$ alkyl group, like, for example, hexylheptamethyltrisiloxane of formula: $(CH_3)_3$—Si—O—Si$(CH_3)(C_6H_{13})$—O—Si$(CH_3)_3$, octylheptamethyltrisiloxane of formula: $(CH_3)_3$—Si—O—Si$(CH_3)(C_8H_{15})$—O—Si$(CH_3)_3$, and mixtures thereof.

The composition according to the invention may advantageously include from 10 to 90% of the total weight of the composition, preferably 40 to 80%, of one or several volatile silicones, relative to the total weight of the composition.

The silicone waxes must be solid or semisolid at ambient temperature. These waxes may be in the form of a paste or of a rigid solid. In particular, these waxes have a melting temperature higher than 25° C. and, preferably, higher than 45° C.

The silicone waxes of the composition of the invention may have the following formula (II):

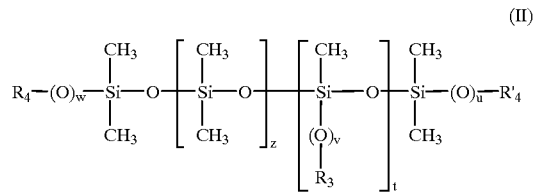

in which $R_3$, $R_4$ and $R'_4$ denote, independently of one another, a methyl group or hydrogen or a linear or branched alkyl chain containing from 10 to 45 carbon atoms, z and t independently denote an integer ranging from 0 to 100, u, v and w independently denote 0 or 1, on condition that t is other than 0 and $R_3$ is other than methyl or hydrogen when $R_4$ and $R'_4$ denote a methyl group or hydrogen and that $R_4$ or $R'_4$ is other than the methyl group or hydrogen when $R_3$ denotes a methyl group or hydrogen or when t has the value 0. In particular, $R_3$, $R_4$ or $R'_4$ each denote a linear chain containing 12 to 35 carbon atoms and, preferably, from 18 to 28 carbon atoms, like, for example, the radicals $C_{16}H_{33}$, $C_{18}H_{37}$, $C_{24}H_{49}$, $C_{26}H_{53}$ or a mixture of these radicals. $R_3$ is preferably an alkyl chain and $R_4$ a methyl group, u, v and w are equal to 0, z has a value of 2 to 40 and t has a value of 45 to 98.

Among the silicone waxes that can be employed in the invention, there may be mentioned behenoxydimethicone (with $R_4$=$CH_3(CH_2)_{21}$, t=0, u=1, w=1, z<10) as sold by Goldschmidt under the name ABIL WAX 2440 (melting temperature of 35° C.), stearyldimethicone (with u=0, v=w=0, $R_4$=$CH_3$ and $R_3$=stearyl) such as that sold by Dow Corning under the name DC 2503, cetyldimethicone (with u=v=w=0, $R_4$=$CH_3$ and $R_3$=cetyl) such as that sold by Goldschmidt under the name ABIL WAX 9814, stearylmethicone (with z=u=w=v=0, $R_4=CH_3$ and $R_3$=stearyl) such as that sold by Goldschmidt under the name ABIL WAX 9809, $C_{24}$–$C_{28}$, alkyldimethicone (with u=v=w=0, $R_4=CH_3$ and $R_3$ is a $C_{24}$–$C_{28}$ alkyl group and z<5) such as that sold by Goldschmidt under the name ABIL WAX 9810 (melting temperature of 60° C.), $C_{30}$–$C_{45}$ alkylmethicone (with z=u=v=w=0, $R_4=CH_3$ and $R_3$=a $C_{30}$–$C_{45}$ alkyl group) such as that sold by Goldschmidt under the name ABIL WAX 9811, and stearoxydimethicone (with z=u=v=w=0, $R_4=CH_3$ and $R_3$=stearyl) such as that sold by Goldschmidt under the name ABIL WAX 2434 (melting temperature of 25° C. and t=10).

It is also possible to employ silicone waxes which $R_4$ and $R'_4$ are a methyl group, u=w=v=0 and the other parameters of the formula and the melting temperature of the wax are given in the table (I) below:

| Reference wax | Z | t | $R_4$ | Melting temperature |
|---|---|---|---|---|
| 1 | 60 | 40 | $C_{16}$ | 30° C. |
| 2 | 95 | 5 | >$C_{30}$ | 60° C. |
| 3 | 90 | 10 | $C_{24}/C_{28}$ | 44° C. |
| 4 | 98 | 2 | $C_{24}/C_{28}$ | 41° C. |
| 5 | 95 | 5 | $C_{24}/C_{28}$ | 39° C. |
| 6 | 60 | 40 | $C_{24}/C_{28}$ | 57° C. |
| 7 | 60 | 40 | >$C_{30}$ | 60° C. |

The composition according to the invention may advantageously include from 2 to 90% of the total weight of the composition, preferably 30 to 70%, of one or more silicone waxes, relative to the total weight of the composition.

Alkyldimethicone copolymers may be mentioned as other silicone waxes which can be employed in the invention. These copolymers are especially those described in documents EP-A-527594, U.S. Pat. No. 5 061 481, U.S. Pat. No. 5 397 566 and EP-A-527594, the disclosures of which are hereby incorporated by reference, and may have the following formula (III):

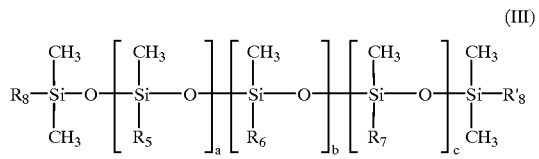

(III)

in which $R_5$, $R_6$, $R_7$, $R_8$ and $R'_8$ denote, independently of one another, a methyl group or hydrogen or a linear or branched alkyl or alkoxy chain containing from 5 to 36 carbon atoms, a and b independently denote an integer ranging from 1 to 50 and c denotes an integer ranging from 0 to 50, on condition that two of the radicals $R_5$, $R_6$, $R_7$, $R_8$ and $R'_8$ are other than a methyl group or hydrogen and differ from one another. In particular, $R_5$ and $R_6$ denote a linear chain which has 10 to 20 carbon atoms, with $R_5$ other than $R_6$, $R_8$ and $R'_8$ are each methyl groups, a ranges from 8 to 18, b ranges from 2 to 12 and c has the value 0.

As copolymers which can be employed in the invention there may be mentioned the copolymers of formula (III) in which c has the value 0 and $R_8$ and $R'_8$ are a methyl group, the other parameters of the formula and the melting temperature of these copolymers being given in the table (II) which follows:

| Co-polymers | $R_5$ | % branching | X | $R_6$ | % branching | y | Melting temperature |
|---|---|---|---|---|---|---|---|
| $C_{01}$ | $C_{14}$ | 6% | 10 | $C_{16}$ | 6% | 10 | — |
| $C_{02}$ | $C_{14}$ | 6% | 10 | $C_{18}$ | 6% | 10 | 26–28° C. |
| $C_{03}$ | $C_{16}$ | 6% | 10 | $C_{16}$–$C_{18}$ | 32% | 10 | — |
| $C_{04}$ | $C_{16}$ | 6% | 10 | $C_{16}$–$C_{18}$ | 32% | 10 | — |
| $C_{05}$ | $C_{16}$ | 6% | 18 | $C_{10}$ | 0% | 2 | 25–27° C. |
| $C_{06}$ | $C_{16}$ | 6% | 16 | $C_{10}$ | 0% | 4 | — |

These copolymers may represent from 0 to 85% of the weight of the composition, and preferably from 2 to 40%.

As a result of their asymmetric structure ($R_1$ different from $R_2$), these copolymers take the form of elastic wax, having intermediate consistency between a wax and gum (polydimethylsiloxane of high molecular weight) which are perfectly miscible with the alkyldimethicones described above. They strengthen the contribution of comfort of the film without detriment to the "nontransfer" property. These copolymers can be employed alone or as a mixture and advantageously in combination with one or more waxes of formula (II). These copolymers can contribute to the hardness of the stick and/or to the cosmetic qualities.

The composition of the invention may furthermore include, in addition to the volatile silicones mentioned above, the fatty substances which are usually employed in the field of application envisaged. As fatty substances there may be mentioned silicones in esterified or unesterified liquid form or in esterified solid form, such as a behenate dimethicone, nonsilicone fatty substances such as oils, pastes and vegetable, mineral, animal and/or synthetic waxes.

Among the nonsilicone fatty substances that may be mentioned are vegetable oils like castor, avocado and jojoba oil, fatty acid esters like isopropyl myristate, alcohols like octyl dodecanol or oleyl alcohol, acetylglycerides, alcohol or polyalcohol octanoates, decanoates or ricinoleates, fatty acid triglycerides like sesame oil, lanolins, hydrocarbons like petroleum, parleam oil and polyisobutene, beeswax, vegetable waxes such as carnauba or candelilla wax, mineral waxes, for example paraffin wax, lignite or microcrystalline waxes or ozokerites, and synthetic waxes like polyethylene waxes.

These silicone or other fatty substances may be selected variously by the person skilled in the art in order to prepare a composition which has the desired properties, for example consistency or texture.

In particular, the composition according to the invention may include at least one of the abovementioned waxes, so as to ensure a good mechanical strength, especially when the composition is in the form of a stick.

In general, the composition may include from 0 to 30% of the total weight of the composition of at least one hydrocarbon wax and preferably from 5 to 25% by weight of hydrocarbon wax.

In addition it has been found that the improvement in the behavior of the composition according to the invention, as well as its absence of migration and/or of transfer, can be particularly advantageous when the composition includes less than 20% by weight of nonvolatile hydrocarbon oil, preferably less than 5% by weight, or even no nonvolatile hydrocarbon oil at all.

The composition of the invention may additionally include any additive usually employed in the field in question, such as antioxidants, perfumes, essential oils, stabilizers, cosmetic active substances, moisturizers, vitamins, essential fatty acids, lipophilic sunscreens, liposoluble polymers, especially hydrocarbon polymers such as polyalkylenes, and polyacrylates. These additives preferably may be present in the composition in a proportion of 0 to 10% of the total weight of the composition.

The person skilled in the art will of course take care to choose the optional additional compounds and/or their quantity in such a way that the advantageous properties of the composition according to the invention are not, or are substantially not, impaired by the envisaged addition.

The compositions according to the invention may be in the form of a stick or a cake, or in the form of a flexible or cast paste, or even in the form of a gelled oily liquid or of a cream.

The composition according to the invention may be in the form of a product for making up the skin, in particular a foundation, a blusher or eyeshadow or, more particularly, a lip rouge. It may also be in an uncolored form, optionally containing cosmetic or dermatological active substances. It can then be employed as a care base for the lips or a fixing base to be applied over a conventional lip rouge. The fixing base then forms a protective film over the film of rouge, which limits its transfer and migration.

The composition of the invention may also be in the form of a dermatological or skin care composition or in the form of a composition more especially for solar protection.

The composition of the invention must, of course, contain a cosmetically or dermatologically acceptable medium, namely a medium capable of being applied to the skin and the mucosae (lips, inside of the eyelids) of human beings.

Another subject of the present invention is a transfer-free anhydrous lip rouge or foundation containing (a) at least one silicone which is volatile at ambient temperature, which at least one silicone comprises a silicone structure and at least one unit containing at least one alkyl chain which is pendent and/or at the end of the silicone structure, wherein the at least one alkyl chain is linear or branched and contains from 3 to 10 carbon atoms, (b) at least one silicone wax which is solid or semisolid at ambient temperature, which at least one silicone wax comprises a silicone structure and at least one unit containing at least one alkyl or alkoxy chain which is pendent and/or at the end of the silicone structure, wherein the at least one chain is linear or branched and contains from 10 to 45 carbon atoms, and (c) pigments and/or fillers.

Another subject of the present invention is the use of the combination of at least one silicone which is volatile at ambient temperature and of at least one silicone wax which is solid or semisolid at ambient temperature, in a composition in order to decrease the transfer and/or the migration of the composition, the at least one volatile silicone comprising a silicone structure and at least one unit containing an alkyl chain which is pendent and/or at the end of the silicone structure, wherein the at least one alkyl chain is linear or branched and contains from 3 to 10 carbon atoms, and the at least one silicone wax comprising a silicone structure and at least one unit containing at least one alkyl or alkoxy chain which is pendent and/or at the end of the silicone structure, wherein the at least one chain is linear or branched and contains from 10 to 45 carbon atoms.

Another subject of the present invention is a method for limiting and/or preventing the transfer of a skin or lip make-up or care composition onto a substrate other than the skin and the lips. The method is drawn to introducing into the composition the combination of at least one silicone which is volatile at ambient temperature and of at least one silicone wax which is solid or semisolid at ambient temperature, in order to decrease the transfer and/or the migration of the composition, the at least one volatile silicone comprising a silicone structure and at least one unit containing at least one alkyl chain which is pendent and/or at the end of the silicone structure, wherein the at least one alkyl chain is linear or branched and contains from 3 to 10 carbon atoms, and the at least one silicone wax comprising a silicone structure and at least one unit containing at least one alkyl or alkoxy chain which is pendent and/or at the end of the silicone structure, wherein the at least one chain is linear or branched and contains from 10 to 45 carbon atoms.

The invention is illustrated in more detail in the following examples, but is not intended to be limited thereby.

EXAMPLE 1

Preparation of Lip Rouge

A lipstick was prepared which had the following composition:

| | |
|---|---|
| hexylheptamethyltrisiloxane | q.s. 100 g |
| stearyldimethicone ($T_m$ = 28° C.) | 23 g |
| polyethylene wax (POLYWAX 500 from Bareco) | 23 g |
| pigments | 8 g |
| natural mothers-of-pearl | 2 g |

The composition was prepared in the usual way, by heating the fatty substances, except the volatile silicone, to 110° C. and by mixing them. The pigments and the fillers were added next and, at 60° C., the volatile oils. The whole was mixed with gentle stirring. The mixture was then cast into suitable molds.

A lipstick was thus obtained, of soft, pleasant texture, which spread well and was applied uniformly. The film was comfortable to wear over time and did not migrate or transfer.

As a comparative test, the above-prepared composition was applied to the left part of the lips of human subjects. For comparison, a lip rouge of the prior art, including no alkylated silicone wax, was applied to the right part of these lips.

The lip rouges were allowed to dry at ambient temperature for 30 minutes and the whole of the lips was then applied onto a sheet of paper. A very faint, barely perceptible, trace of lip rouge was found on all the sheets of paper, both in the case of the composition of the invention and of the composition of the prior art. However, the film obtained on the lips with the composition of the invention was more comfortable and less dry than that obtained with the composition of the prior art.

EXAMPLE 2

Preparation of Lip Rouge

A lipstick was prepared which had the following composition:

| | |
|---|---|
| hexylheptamethyltrisiloxane | q.s. 100 g |
| ABIL WAX 9810 | 25 g |
| silicone, fluid at ambient temperature (ABIL WAX 9801) | 5 g |
| pigments | 8 g |
| titanium mica | 2 g |

This composition was prepared in the usual way, by heating the fatty substances to 95° C. and then adding the pigments and the mothers-of-pearl except for the volatile silicone, and by mixing the whole. The volatile silicone was then added at 60° C. and the whole was then mixed. This mixture was then cast into suitable packages.

A hard stick was thus obtained, with a pleasant texture, which spread well and which was applied uniformly. The film obtained on the lips was comfortable to wear over time and did not migrate.

EXAMPLE 3

Preparation of Fixing Base for Lip Rouge

A fixing base for lip rouge which had the following composition was prepared:

| | |
|---|---|
| octylheptamethyltrisiloxane | q.s. 100 g |
| ABIL WAX 9810 | 30 g |
| polyethylene waxes (POLY WAX 500 from Bareco) | 10 g |
| fillers (nylon powder) | 5 g |

The composition was prepared according to Example 1.

A fixing base was obtained in stick form. This base had a pleasant texture and was applied easily to a film of conventional lip rouge. It made it possible to avoid the migration and the transfer of the conventional film of lip rouge onto a substrate such as a glass.

EXAMPLE 4

Preparation of Cast Foundation

A foundation which had the following composition was prepared:

| | |
|---|---|
| stearyldimethicone (silicone wax of $T_m$ = 35–40° C.) | 13.5 g |
| hexylheptamethyltrisiloxane | q.s. 100 g |
| pigments | 16.2 g |
| fillers (ORGASOL) | 16.7 g |
| stabilizers | q.s. |

The wax was melted and the other constituents were then introduced in the following order: pigments, fillers, stabilizers, and the volatile silicone, and the whole was mixed. The mixture was then cast into suitable molds.

A "nontransfer" cast foundation was obtained which could be spread with a sponge, was of great softness and easy to spread.

What is claimed is:

1. A transfer-free make-up or care composition comprising (a) at least one silicone which is volatile at ambient temperature, said at least one silicone comprising a silicone structure and at least one unit containing at least one alkyl chain which is pendent or at the end of said silicone structure, said at least one alkyl chain being linear or branched and having from 3 to 10 carbon atoms, wherein said at least one silicone which is volatile at ambient temperature has the formula (I):

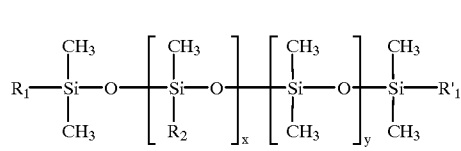

in which $R_1$, $r'_1$ and $R_2$ denote, independently of one another, a methyl group, hydrogen, or a linear or branched chain having from 3 to 10 carbon atoms, x and y independently denote an integer ranging from 0 to 10, with the proviso that x is other than 0 when $R_1$ and $R'_1$ denote a methyl group or hydrogen and $R_2$ is other than methyl or hydrogen, and that $R_1$ or $R'_1$ is other than a methyl group or hydrogen when $R_2$ denotes a methyl group or hydrogen or when x has the value 0;

(b) at least one silicone wax which is solid or semisolid at ambient temperature, said at least one silicone wax comprising a silicone structure and at least one unit containing at least one alkyl or alkoxy chain which is pendent or at the end of said silicone structure, said at least one alkyl or alkoxy chain being linear or branched and having from 10 to 45 carbon atoms, wherein said at least one silicone wax has the formula (II):

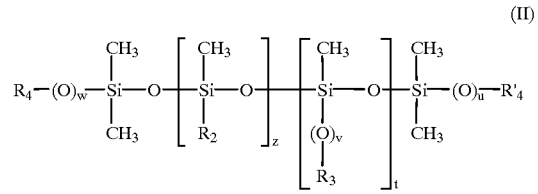

in which $R_3$, $R_4$ and $R'_4$ denote, independently of one another, a methyl group, hydrogen or a linear or branched alkyl chain containing from 10 to 45 carbon atoms, z and t independently denote an integer ranging from 0 to 100, u, v and w independently denote 0 or 1, with the proviso that t is other than 0 and $R_3$ is other than methyl or hydrogen when $R_4$ and $R'_4$ denote a methyl group or hydrogen and that $R_4$ or $R'_4$ is other than the methyl group or hydrogen when $R_3$ denotes a methyl group or hydrogen or when t has the value 0, wherein the combination of said at least one volatile silicone containing said $C_3$ to $C_{10}$ alkyl chain and at least one said silicone wax containing said $C_{10}$ to $C_{45}$ alkyl or alkoxy chain results in a transfer-free film which is comfortable on the skin or the lips.

2. A composition according to claim 1, wherein said composition is in anhydrous form.

3. A composition according to claim 1, wherein said at least one volatile silicone is present in an amount of from 10 to 90% by weight of the total weight of the composition.

4. A composition according to claim 3, wherein said at least one volatile silicone is present in an amount of from 40 to 80% by weight of the total weight of the composition.

5. A composition according to claim 1, wherein said at least one volatile silicone has a $C_3$–$C_{10}$ pendent alkyl chain.

6. A composition according to claim 1, wherein said at least one volatile silicone has a $C_7$–$C_{10}$ alkyl end chain.

7. A composition according to claim 1, wherein said at least one volatile silicone is hexylheptamethyltrisiloxane, octylheptamethyltrisiloxane or a mixture thereof.

8. A composition according to claim 1, wherein said at least one silicone wax is a wax of formula (II) in which $R_3$, $R_4$ or $R'_4$ is a radical $C_{16}H_{33}$, $C_{18}H_{37}$, $C_{24}H_{49}$ or $C_{26}H_{53}$ or a mixture of any of these radicals.

9. A composition according to claim 1, wherein said at least one silicone wax is present in an amount of from 2 to 90% of the total weight of the composition.

10. A composition according to claim 9, wherein said at least one silicone wax is present in an amount of from 30 to 70% of the total weight of the composition.

11. A composition according to claim 1, said composition further comprising at least one nonvolatile hydrocarbon oil present in an amount of less than 5% of the total weight of the composition.

12. A composition according to claim 1, said composition further comprising hydrocarbon wax in an amount of from 0 to 30% of the total weight of the composition.

13. A composition according to claim 12, said composition further comprising hydrocarbon wax in an amount of from 5 to 25% of the total weight of the composition.

14. A composition according to claim 1, said composition further comprising a particulate phase in an amount of from 0 to 35% of the total weight of the composition.

15. A composition according to claim 14, said composition further comprising a particulate phase in an amount of from 5 to 25% of the total weight of the composition.

16. A composition according to claim 1, wherein said composition is in the form of a stick, a cake, a flexible or cast paste, a cream or a gel.

17. A composition according to claim 1, wherein said composition additionally contains a cosmetic or dermatological active substance.

18. A composition according to claim 1, wherein said composition is in the form of a foundation, blusher or eyeshadow composition or a lip rouge, a care base or a fixing base for the lips, a skin care product or a composition for solar protection.

19. A composition according to claim 1, wherein said composition further comprises at least one silicone copolymer of formula (III):

$$\text{(III)} \quad R_8-\underset{\underset{CH_3}{|}}{\overset{\overset{CH_3}{|}}{Si}}-O-\left[\underset{\underset{R_5}{|}}{\overset{\overset{CH_3}{|}}{Si}}-O\right]_a\left[\underset{\underset{R_6}{|}}{\overset{\overset{CH_3}{|}}{Si}}-O\right]_b\left[\underset{\underset{R_7}{|}}{\overset{\overset{CH_3}{|}}{Si}}-O\right]_c\underset{\underset{CH_3}{|}}{\overset{\overset{CH_3}{|}}{Si}}-R'_8$$

in which
$R_5$, $R_6$, $R_7$, $R_8$ and $R'_8$ denote, independently of one another, a methyl group, hydrogen, or a linear or branched alkyl or alkoxy chain having from 5 to 36 carbon atoms,
a and b independently denote an integer ranging from 1 to 50, and
c denotes an integer ranging from 0 to 50, with the proviso that two of the radicals $R_5$, $R_6$, $R_7$, $R_8$ and $R'_8$ are other than a methyl group or hydrogen and differ from one another.

20. A composition according to claim 19, wherein said at least one copolymer of formula (III) represents from 0 to 85% of the total weight of the composition.

21. A composition according to claim 20, wherein said at least one copolymer of formula (III) represents from 2 to 40% of the total weight of the composition.

22. A transfer-free anhydrous lip rouge or foundation comprising (a) at least one silicone which is volatile at ambient temperature, said at least one silicone comprising a silicone structure and at least one unit containing at least one alkyl chain which is pendent or at the end of said silicone structure, said at least one alkyl chain being linear or branched and having from 3 to 10 carbon atoms, wherein said at least one silicone which is volatile at ambient temperature has the formula (I):

$$\text{(I)} \quad R_1-\underset{\underset{CH_3}{|}}{\overset{\overset{CH_3}{|}}{Si}}-O-\left[\underset{\underset{R_2}{|}}{\overset{\overset{CH_3}{|}}{Si}}-O\right]_x\left[\underset{\underset{CH_3}{|}}{\overset{\overset{CH_3}{|}}{Si}}-O\right]_y\underset{\underset{CH_3}{|}}{\overset{\overset{CH_3}{|}}{Si}}-R'_1$$

in which
$R_1$, $R'_1$ and $R_2$ denote, independently of one another, a methyl group, hydrogen, or a linear or branched chain having from 3 to 10 carbon atoms,
x and y independently denote an integer ranging from 0 to 10, with the proviso that x is other than 0 when $R_1$ and $R'_1$ denote a methyl group or hydrogen and $R_2$ is other than methyl or hydrogen, and that $R_1$ or $R'_1$ is other than a methyl group or hydrogen when $R_2$ denotes a methyl group or hydrogen or when x has the value 0, wherein said at least one silicone is present in an amount of from 10 to 90% by weight of the total weight of the composition;

(b) at least one silicone wax which is solid or semisolid at ambient temperature, said at least one silicone wax comprising a silicone structure and at least one unit containing at least one alkyl or alkoxy chain which is pendent or at the end of said silicone structure, said at least one alkyl or alkoxy chain being linear or branched and having from 10 to 45 carbon atoms.

wherein said at least one silicone wax has the formula (II):

$$\text{(II)} \quad R_4-(O)_w-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_z\left[\underset{\underset{(O)_v}{|}\atop\underset{R_3}{|}}{\overset{\overset{CH_3}{|}}{Si}}-O\right]_t\underset{\underset{CH_3}{|}}{\overset{\overset{CH_3}{|}}{Si}}-(O)_u-R'_4$$

in which
$R_3$, $R_4$ and $R'_4$ denote, independently of one another, a methyl group, hydrogen or a linear or branched alkyl chain containing from 10 to 45 carbon atoms,
z and t independently denote an integer ranging from 0 to 100,
u, v and w independently denote 0 or 1, with the proviso that t is other than 0 and $R_3$ is other than methyl or hydrogen when $R_4$ and $R'_4$ denote a methyl group or hydrogen and that $R_4$ or $R'_4$ is other than the methyl group or hydrogen when $R_3$ denotes a methyl group or hydrogen or when t has the value 0,
wherein the combination of said at least one volatile silicone containing said $C_3$ to $C_{10}$ alkyl chain and said at least one silicone wax containing said $C_{10}$ to $C_{45}$ alkyl or alkoxy chain results in a transfer-free film which is comfortable on the skin or the lips, and (c) at least one pigment or filler.

23. A method for preparing a composition for decreasing the transfer or migration of a composition, said method comprising combining at least one silicone which is volatile at ambient temperature with at least one silicone wax which is solid or semisolid at ambient temperature, wherein said at least one volatile silicone comprises a silicone structure and at least one unit containing an alkyl chain which is pendent or at the end of said silicone structure, said at least one alkyl chain being linear or branched and having from 3 to 10 carbon atoms, wherein said at least one silicone which is volatile at ambient temperature has the formula(I):

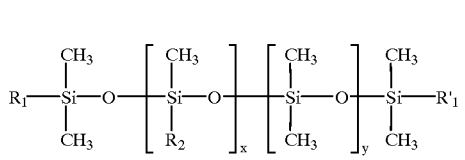

in which $R_1$, $R'_1$ and $R_2$ denote, independently of one another, a methyl group, hydrogen, or a linear or branched chain having from 3 to 10 carbon atoms, x and y independently denote an integer ranging from 0 to 10, with the proviso that x is other than 0 when $R_1$ and $R'_1$ denote a methyl group or hydrogen and $R_2$ is other than methyl or hydrogen, and that $R_1$ or $R'_1$ is other than a methyl group or hydrogen when $R_2$ denotes a methyl group or hydrogen or when x has the value 0, and wherein the at least one silicone wax comprises a silicone structure and at least one unit containing at least one alkyl or alkoxy chain which is pendent or at the end of said silicone structure, said at least one chain being linear or branched and having from 10 to 45 carbon atoms, wherein said at least one silicone wax has the formula (II):

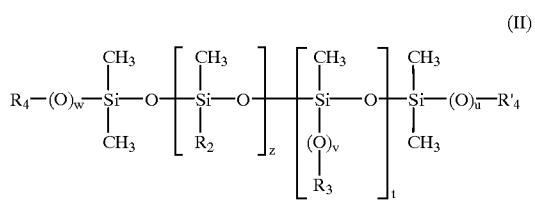

in which $R_3$, $R_4$ and $R'_4$ denote, independently of one another, a methyl group, hydrogen or a linear or branched alkyl chain containing from 10 to 45 carbon atoms, z and t independently denote an integer ranging from 0 to 100, u, v and w independently denote 0 or 1, with the proviso that t is other than 0 and $R_3$ is other than methyl or hydrogen when $R_4$ and $R'_4$ denote a methyl group or hydrogen and that $R_4$ or $R'_4$ is other than the methyl group or hydrogen when $R_3$ denotes a methyl group or hydrogen or when t has the value 0, wherein the combination of said at least one volatile silicone containing said $C_3$ to $C_{10}$ alkyl chain and said at least one silicone wax containing said $C_{10}$ to $C_{45}$ alkyl or alkoxy chain results in a transfer-free film which is comfortable on the skin or the lips.

24. A method according to claim 23, wherein said at least one volatile silicone is present in an amount of from 10 to 90% by weight of the total weight of the composition.

25. A method according to claim 24, wherein said at least one volatile silicone is present in an amount of from 40 to 80% by weight of the total weight of the composition.

26. A method according to claim 23, wherein said at least one volatile silicone has a $C_3$–$C_{10}$ pendent alkyl chain.

27. A method according to claim 23, wherein said at least one volatile silicone has a $C_7$–$C_{10}$ alkyl end chain.

28. A method according to claim 23, wherein said at least one volatile silicone is hexylheptamethyltrisiloxane, octylheptamethyltrisiloxane or a mixture thereof.

29. A method according to claim 23, wherein said at least one silicone wax is a wax of formula (II) in which $R_3$, $R_4$ or $R'_4$ is a radical $C_{16}H_{33}$, $C_{18}H_{37}$, $C_{24}H_{49}$ or $C_{26}H_{53}$ or a mixture of any of these radicals.

30. A method according to claim 23, wherein said at least one silicone wax is present in an amount of from 2 to 90% of the total weight of the composition.

31. A method according to claim 30, wherein said at least one silicone wax is present in an amount of from 30 to 70% of the total weight of the composition.

32. A method according to claim 23, said composition further comprising hydrocarbon wax in an amount of from 0 to 30% of the total weight of the composition.

33. A method according to claim 32, said composition further comprising hydrocarbon wax in an amount of from 5 to 25% of the total weight of the composition.

34. A method according to claim 23, said composition further comprising a particulate phase in an amount of from 0 to 35% of the total weight of the composition.

35. A method according to claim 34, said composition further comprising a particulate phase in an amount of from 5 to 25% of the total weight of the composition.

36. A method according to claim 23, wherein said composition is in the form of a stick, a cake, a flexible or cast paste, a cream or a gel.

37. A method according to claim 23, wherein said composition further comprises a cosmetic or dermatological active substance.

38. A method according to claim 23, wherein said composition is in the form of a foundation, blusher or eyeshadow or lip rouge composition, a care base or a fixing base for the lips, a skin care product or a solar composition.

39. A method according to claim 23, wherein said composition further comprises at least one silicone copolymer of formula (III):

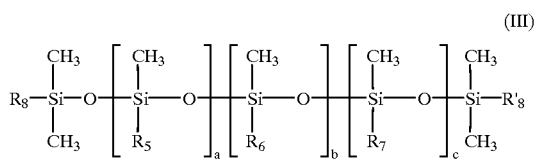

in which $R_5$, $R_6$, $R_7$, $R_8$ and $R'_8$ denote, independently of one another, a methly group, hydrogen or a linear or branched alkyl or alkoxy chain containing from 5 to 36 carbon atoms, a and b independently denote an integer ranging from 1 to 50, and c denotes an integer ranging from 0 to 50, with the proviso that two of the radicals $R_5$, $R_6$, $R_7$, $R_8$ and $R'_8$ are other than a methyl group or hydrogen and differ from one another.

40. A method according to claim 39, wherein said at least one copolymer of formula (III) represents from 0 to 85% by weight of the total weight of the composition.

41. A method according to claim 40, wherein said at least one copolymer of formula (III) represents from 2 to 40% by weight of the total weight of the composition.

42. A method according to claim 39, wherein said at least one composition is anhydrous.

43. A method for decreasing transfer or migration of a skin, lip make-up or care composition onto a substrate other than said skin or said lips, said method comprising introducing into said composition a combination of at least one silicone which is volatile at ambient temperature and at least one silicone wax which is solid or semisolid at ambient temperature to decrease the transfer or the migration of said composition, said at least one volatile silicone comprising a silicone structure and at least one unit containing an alkyl chain which is pendent or at the end of said silicone structure, said at least one alkyl chain being linear or branched and having from 3 to 10 carbon atoms, wherein said at least one silicone which is volatile at ambient temperature has the formula (I):

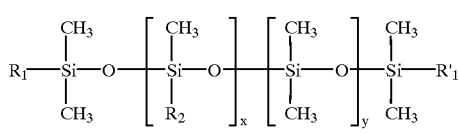

in which

R$_1$, R'$_1$ and R$_2$ denote, independently of one another, a methyl group, hydrogen, or a linear or branched chain having from 3 to 10 carbon atoms, x and v independently denote an integer ranging from 0 to 10, with the proviso that x is other than 0 when R$_1$ and R'$_1$ denote a methyl group or hydrogen and R$_2$ is other than methyl or hydrogen, and that R$_1$ or R'$_1$ is other than a methyl group or hydrogen when R$_2$ denotes a methyl group or hydrogen or when x has the value 0, and said at least one silicone wax comprising a silicone structure and at least one unit containing at least one alkyl or alkoxy chain which is pendent or at the end of said silicone structure, said at least one chain being linear or branched and having from 10 to 45 carbon atoms, wherein said at least one silicone wax has the formula (II):

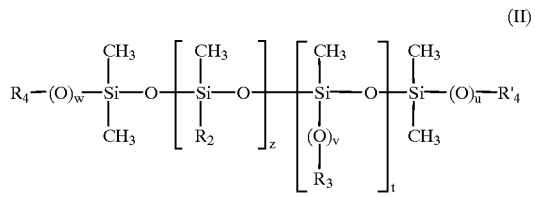

in which

R$_3$, R$_4$ and R'$_4$ denote, independently of one another, a methyl group, hydrogen or a linear or branched alkyl chain containing from 10 to 45 carbon atoms, z and t independently denote an integer ranging from 0 to 100, u, v and w independently denote 0 or 1, with the proviso that t is other than 0 and R$_3$ is other than methyl or hydrogen when R$_4$ and R'$_4$ denote a methyl group or hydrogen and that R$_4$ or R'$_4$ is other than the methyl group or hydrogen when R$_3$ denotes a methyl group or hydrogen or when t has the value 0, wherein the combination of said at least one volatile silicone containing said C$_3$ to C$_{10}$ alkyl chain and said at least one silicone wax containing said C$_{10}$ to C$_{45}$ alkyl or alkoxy chain results in a transfer-free film which is comfortable on the skin or the lips, and applying said composition to said skin or lips.

* * * * *

UNITED STATES PATENT AND TRADEMARK OFFICE
CERTIFICATE OF CORRECTION

PATENT NO. : 5,972,318
DATED : October 26, 1999
INVENTOR(S) : Isabelle BARA

It is certified that error appears in the above-identified patent and that said Letters Patent is hereby corrected as shown below:

Claim 1, col. 10, line 10, "$r'_1$," should read -- $R'_1$ --.

Claim 22, col. 12, line 18, "$r_1$" should read -- $R_1$ --.

Claim 43, col. 15, line 29, "x and v" should read -- x and y --.

Signed and Sealed this

Sixth Day of June, 2000

*Attest:*

Q. TODD DICKINSON

*Attesting Officer*  *Director of Patents and Trademarks*